(12) United States Patent
Cahana et al.

(10) Patent No.: US 9,783,517 B2
(45) Date of Patent: *Oct. 10, 2017

(54) METHOD FOR SYNTHESIS OF AN OUTPUT INCLUDING DIESTERS OF 5-METHYL-2-FUROIC ACID

(71) Applicants: Aviad Cahana, Albuquerque, NM (US); Tim Martin, Albuquerque, NM (US)

(72) Inventors: Aviad Cahana, Albuquerque, NM (US); Tim Martin, Albuquerque, NM (US)

(73) Assignee: XF Technologies Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,139

(22) Filed: Mar. 18, 2015

(65) Prior Publication Data
US 2015/0203462 A1    Jul. 23, 2015

Related U.S. Application Data

(63) Continuation-in-part of application No. 14/195,513, filed on Mar. 3, 2014, now Pat. No. 9,102,644, which is a continuation-in-part of application No. PCT/US2013/057795, filed on Sep. 3, 2013, application No. 14/661,139, which is a continuation-in-part of application No. 14/192,828, filed on Feb. 27, 2014, now Pat. No. 9,108,940, which
(Continued)

(51) Int. Cl.
C07D 307/68 (2006.01)
C07D 307/48 (2006.01)
C07D 307/50 (2006.01)

(52) U.S. Cl.
CPC ......... *C07D 307/68* (2013.01); *C07D 307/48* (2013.01); *C07D 307/50* (2013.01)

(58) Field of Classification Search
CPC ... C07D 307/48; C07D 307/50; C07D 307/68
See application file for complete search history.

(56) References Cited

U.S. PATENT DOCUMENTS 8,710,250 B2 * 4/2014 Mikochik ............ C07D 307/68
549/484
9,108,940 B2 * 8/2015 Mikochik ............ C07D 307/68

* cited by examiner

*Primary Examiner* — Valerie Rodriguez-Garcia
(74) *Attorney, Agent, or Firm* — V. Gerald Grafe (57) ABSTRACT

The present invention describes methods and apparatuses for the synthesis of 5-(chloromethyl)-2-furaldehyde (CMF) from saccharides in pure or crude form, the method comprising: (a) continuously contacting saccharides in pure or crude form, hydrochloric acid, and an organic solvent, by way of a continuous, biphasic-flow reactor assembly at a temperature from about 60 degrees C. to about 200 degrees C. and pressures from about 1 atmosphere to about 20 atmospheres, such that CMF is produced; (b) separating 5-(chloromethyl)-2-furaldehyde by liquid/liquid and solid/liquid phase separation; (c) producing at least five kilograms per day with at least 50% yield. Embodiments of the present invention can produce CMF in a continuous fashion, with high yield and without degradation of CMF to such side products as 5-(hydroxymethyl)furfural (HMF), 2-(2-hydroxyacetyl)furan (HAF) and levulinic acid (LA).

4 Claims, 10 Drawing Sheets

Related U.S. Application Data is a continuation of application No. 13/817,452, filed as application No. PCT/US2011/048009 on Aug. 17, 2011, now Pat. No. 8,710,250.

(60) Provisional application No. 61/818,418, filed on May 1, 2013, provisional application No. 61/714,225, filed on Oct. 16, 2012, provisional application No. 61/375,189, filed on Aug. 19, 2010, provisional application No. 61/375,367, filed on Aug. 20, 2010.

Glucose

Furan

Hydroxymethyl fufural (HMF)

Chloromethyl fufural (CMF)

Fig. 10

METHOD FOR SYNTHESIS OF AN OUTPUT INCLUDING DIESTERS OF 5-METHYL-2-FUROIC ACID

CROSS REFERENCE TO RELATED APPLICATIONS

This application claims priority as a continuation-in-part of U.S. Ser. No. 14/195,513, filed Mar. 3, 2014; and thence to its priority applications, U.S. Ser. No. 14/195,513 claimed priority as a continuation in part of PCT/US2013/057795, filed 3 Sep. 2013; and to U.S. provisional 61/818,418, filed 1 May 2013; and to U.S. provisional 61/714,225, filed 16 Oct. 2012; each of which were claimed for priority by PCT/US2013/057795. This application further claims priority as a continuation-in-part of U.S. Ser. No. 14/192,828, filed Feb. 27, 2014; and thence to its priority applications, U.S. Ser. No. 14/192,828 claimed priority as a continuation of U.S. Ser. No. 13/817,452, filed Mar. 5, 2013; and thence to its priority applications; U.S. Ser. No. 13/817,452 was a 371 of PCT/US11/48009, filed Aug. 17, 2011; which claimed benefit of U.S. provisional 61/375,367, filed Aug. 20, 2010, and U.S. provisional 61/375,189, filed Aug. 19, 2010. Each of the foregoing is incorporated herein by reference.

BACKGROUND 5-(chloromethyl)-2-furaldehyde (CMF) is a furan based platform chemical derived from six carbon carbohydrates by the action of concentrated hydrochloric acid. CMF has been the subject of numerous publications concerning both its formation from biomass, as well as its use as a flexible platform molecule for creating specialty fuel and fuel products. While the chemistry of producing halogenated methyl furfurals had been examined (see, e.g., M. Mascal, U.S. Pat. No. 7,829,732 B2, 2010) a production scale system for producing CMF from saccharides in a pure or crude form has not yet been described.

The formation of CMF from cellulosic and hemi-cellulosic biomass (saccharides in a pure or crude form) also yields a by-product, which has been identified as a precursor to Hydrothermal Carbon (HTC), or Hydrothermal Carbon (HTC) itself. The size of HTC particles range from about 5 nm to about tens of micrometers (agglomerated) in diameter. When producing CMF, these particulates reside in both aqueous and organic phases of the reaction medium, making isolation of pure CMF difficult.

A practical, but not production scale, continuous flow system for creating CMF has been described by Brasholz (see, e.g., M. Brasholz, K. von Känel, C. H. Hornung, S. Saubern and J. Tsanaktsidis, Green Chem., 2011, 13, 1114); however, this study did not address the scale and repeatability limitations that prevent such a system from being utilized as a production scale system. The system described in Brasholz includes several limitations that are addressed in the present invention.

Mascal in US 2009/0234142 describes a method of producing CMF. Mascal teaches a batch reaction, wherein polysaccharide and an aqueous acid are introduced to a reaction vessel, and then organic solvent is added continuously to the vest. Mascal accordingly teaches a method that allows continuous extraction of formed products from a batch reaction. All of Mascal's examples teach the batch reaction proceeding for 30 hours, while reaction products are removed and organic solvent is added either continuously or at intervals of from 1 minute to 12 hours. Mascal teaches a single step of cooling a reaction mixture for preparing HMF from CMF. Mascal, in an example of production of 5-methylfurfural, teaches the use of aqueous sodium bicarbonate to quench previously added hydrochloric acid. Mascal's methods unavoidably produce 5-(hydroxymethyl)furfural (HMF), 2-(2-hydroxyacetyl)furan (HAF) and levulinic acid (LA) as by products of the degradation of CMF.

DESCRIPTION OF INVENTION

The present invention describes methods and apparatuses for the synthesis of CMF from saccharides in a pure or crude form. Example methods according to the present invention comprise: (a) contacting saccharides in a pure or crude form, hydrochloric acid, and an organic solvent, by way of a continuous, biphasic-flow reactor assembly at a temperature from about 60 degree C. to about 200 degree C. and pressures from about 1 atm to 10 atm, such that CMF is produced; (b) separating 5-(chloromethyl)-2-furaldehyde (CMF) by liquid/liquid and solid/liquid phase separation; (c) producing at least five kilograms per day with at least 50% yield.

The present invention provides various advantages over the prior art, including as an example the teaching of Brasholz. As an example, the filter described in Brasholz will clog and become inoperable after approximately one hour of operation due to the formation of HydroThermal Carbon (HTC) by-products on scales larger than described in their invention. By immediately cooling the reaction medium after reaction by means of a heat remover as taught herein, HTC formation is attenuated. As another example, following liquid/liquid extraction of the organic phase containing CMF from the aqueous acid phase, a washing of the organic phase with a basic aqueous solution, as taught herein, serves to further enhance the yield of CMF, and also reduces organic-soluble HTC.

In some example embodiments, the invention provides a method for the synthesis of an output consisting of one or more of: an ester of 5-methyl-2-furoic acid, an amide of 5-methyl-2-furoic acid, and a thioester of 5-methyl-2-furoic acid, from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system.

In some example embodiments, the reactive nucleophile is poly(vinyl alcohol) or a polymer composition containing poly(vinyl alcohol); and the output consists of an ester of 5-methyl-2-furoic acid having an alkoxycarbonyl portion; and the alkoxycarbonyl portion is poly(vinyl alcohol) or a polymer composition containing poly(vinyl alcohol).

In some example embodiments, the reactive nucleophile comprises one or more of (1) a linear aliphatic diol, (2) a branched aliphatic diol, and (3) a cyclic aliphatic diol; containing between 1 and 8 carbon atoms. Examples include, without limitation, ethylene glycol, propylene glycol, diethylene glycol, and triethylene glycol.

In some example embodiments, the reactive nucleophile comprises one or more of (1) a linear aliphatic diol, (2) a branched aliphatic diol, and (3) a cyclic aliphatic diol; containing between 1 and 8 carbon atoms.

In some example embodiments, the output consists of a diester of 5-methyl-2-furoic acid having an alkoxycarbonyl portion; and the alkoxycarbonyl portion comprises one or more of (1) a linear aliphatic chain, (2) a branched aliphatic chain and (3) a cyclic aliphatic; derived from a diol or glycol containing between 2 and 8 carbon atoms.

In some example embodiments, the reactive nucleophile comprises a silanol.

BRIEF DESCRIPTION OF THE DRAWINGS

The accompanying drawings, which are incorporated in and form part of the specification, illustrate the present invention and, together with the description, describe the invention.

MODES FOR CARRYING OUT THE INVENTION AND INDUSTRIAL APPLICABILITY

Definitions

In the description of the invention herein, various terms are used as described below. Saccharides in a pure or crude form—The term "saccharide" refers to a sugar, such as a monosaccharide, a disaccharide, an oligosaccharide or a polysaccharide and any combination thereof. "Saccharides in a crude form" refers to monosaccharide based biomass, a disaccharide based biomass, an oligosaccharide based biomass or a polysaccharide based biomass. Biomass is biological material derived from living, or recently living organisms. It most often refers to plants or plant-derived materials which are specifically called lignocellulosic biomass.

Phase separation—Describing separation of solid from liquid by filtration through a semi-porous medium, by way of gravity, vacuum, or mechanical force, such that the solid is retained by the semi-porous medium; can describe separation of liquid from liquid relying on differences in density, by gravity or mechanical force, including the addition of fresh solvent to remove further product from solution.

Size exclusion separation—Using a medium to separate solids from liquid based on solid particle size.

Continuous Flow—Comprises continuous provision of all parts of the process, that include, but not limited to, addition of starting materials, reaction itself, contact with heat removal devise, communication between parts of the setup, phase separation, base wash, filtration, solvent removing, and recovering chemicals, participating in the process. Practiced without substantial interruption or break, but not necessarily constantly.

Continuous Extraction—Describing a method of separation either by liquid/liquid methods, or solid/liquid methods being practiced without substantial interruption or break, but not necessarily constantly.

Base Wash/basic wash—Using an inorganic base dissolved in water to treat CMF dissolved in an organic phase, in order to neutralize or raise pH greater than or equal to seven, and separating HTC from the organic phase. This will decrease CMF degradation under conditions of the reaction and stabilize CMF in organic phase for further processing. This process is diagramed in FIG. 6.

Biphasic—Having two distinct visible liquid layers, which are immiscible due to differences in polarity, acidity, or density. In some cases two layers of biphasic system can be distinguished by the means of proper device.

Hydrothermal Carbon (HTC)—Carbonaceous material agglomerated under hydro (water) thermal (elevated temperatures) conditions, which can be soluble under both aqueous and organic environments.

Yield—Chemical yield of the product from the starting saccharides in a pure or crude form. The chemical yield can be provided in units of grams or moles, but is always based on the amount of saccharides in a pure or crude form in the starting material and is used to determine the chemical yield of the CMF.

While the chemistry of producing halogenated furfurals has been examined (see, e.g., M. Mascal, U.S. Pat. No. 7,829,732 B2, 2010, incorporated herein by reference), a production scale system for producing CMF from saccharides in a pure or crude form has not yet been described. A previously described practical, but not production scale, continuous flow system creating CMF has been described (see, e.g., M. Brasholz, K. von Känel, C. H. Hornung, S. Saubern and J. Tsanaktsidis, Green Chem., 2011, 13, 1114, incorporated herein by reference); however, this study did not address the scale and repeatability limitations that prevent such a system from being utilized as a production scale system.

First, the filter described in Brasholz will clog and become inoperable after approximately one hour of operation due to the formation of HTC by-products on scales larger than described in their invention. By immediately cooling the reaction medium after reaction by means of a heat remover, HTC formation is attenuated. Second, following liquid/liquid extraction of the organic phase containing CMF from the aqueous acid phase, a washing of the organic phase with a basic aqueous solution serves to further enhance the yield of CMF, and also removes organic-soluble HTC.

The present invention addresses these issues and provides the design and the process of a continuous flow, biphasic reaction apparatus for efficient, high yield CMF production. CMF production includes a major four-stage process: contacting the reactants in a suitable environment, followed by filtration, phase separation and post production treatment to prevent degradation, as was mentioned in [1,7]. As used herein, the term "yield" refers to the chemical yield of the product from the starting saccharides in a pure or crude form. The chemical yield can be provided in units of grams or moles, but is based on the amount of saccharides in a pure or crude form in the starting material and is used to determine the chemical yield of the CMF and other furanic products.

In the first stage of this process, saccharides in a pure or crude form, hydrochloric acid, and an organic solvent (or mixture of solvents) are contacted by way of a continuous, biphasic-flow reactor assembly at a temperature from about 60 degree C. to about 200 degree C. and pressures from about 1 atmospheres to 20 atmospheres, such that CMF is produced.

Saccharides in a pure or crude form suitable for this process include any six-carbon containing, ketose and aldose isomers and diastereomers of glucose and fructose, including but not limited to mannose, glucose, galactose, sorbose, psicose, tagatose, allose, altrose, idose, and talose, and any combination thereof. These saccharides in a pure or crude form can be in dry form, in paste form, or dissolved in a suitable solvent, such as water.

Hydrochloric acid refers to aqueous solutions of hydrogen chloride gas. Useful concentrations of hydrochloric acid for the present invention are from 1% to 38%, or from 26% to 38%. In some embodiments, preferred concentrations are from 30% to 36%. The hydrochloric acid useful in the present invention can contain inorganic salts, such as metal halides, lithium chloride or sodium chloride, as well as mineral acids, including sulfuric acid and hydrobromic acid.

Organic solvents refer to carrier fluids which are immiscible with water. Organic solvents useful in the present invention include, but are not limited to, dichloromethane, chloroform, carbon tetrachloride, diethyl ether, dipropyl ether, ethyl acetate, hexanes, dichloroethane and its isomers, trichloroethane and its isomers, toluene, benzene, and xylenes. Preferred organic solvents for this invention include those with densities greater than the hydrochloric acid, including dichloromethane, chloroform, 1,2-dichloroethane, and other halogenated organic solvents and mixtures of solvents useful for this process.

Temperatures useful in the present invention range from 60 degrees C. to 200 degrees C., preferably from 80 degrees C. to 120 degrees C.

Pressures useful in the present invention range from 1 atmosphere to 20 atmospheres, preferably from 1 atmospheres to 10 atmospheres.

Reaction times useful for the present invention are from 1 second to 24 hours, preferably between 1 minute and 25 minutes, most preferably between 5 minutes and 15 minutes.

In the present invention, the flow of organic and aqueous phase liquids is continuous from exiting the pump until reaching the receiving vessel. Used in the present invention the term "continuous" will be used as meaning practiced without substantial interruption or break, but not necessarily constantly.

In order to achieve high pressures and temperatures to allow for high efficiency conversion of saccharides in a pure or crude form to 5-(chloromethyl)-2-furaldehyde, the organic phase and hydrochloric acid to be pressurized mechanically using a metered chemical delivery apparatus, or similar device that is capable of creating pressures at varying speed for a sustained amount of time.

In the second stage of the process, the biphasic reaction mixture is constantly contacted with a heat remover device and is cooled to between 30 degrees C. to 40 degrees C. Suitable heat exchange devices for this invention include ice baths, heat sinks, and heat exchange pumps with coolant fluid. Once cooled to between 30 degrees C. and 40 degrees C., the biphasic reaction mixture is continuously subjected to solid/liquid phase separation through a semi-porous membrane, by the action of vacuum, gravity, or mechanical force. Semi-porous membranes useful in this invention include, but are not limited to, glass frit funnels, cellulose paper filters, silica gel, alumina, sand, sock-type filters made out of plastic polymers (i.e.—polyethylene, polypropylene, Teflon, etc.), or combinations thereof. In this manner, insoluble HTC can be continuously removed and dried for disposal or use in other applications.

In the third stage of the process, liquid/liquid phase separation of the biphasic mixture can occur in a continuous, semi-continuous, or batch manner. At liquid/liquid phase separation, the organic phase containing CMF can be concentrated to reduce total volume through simple distillation or vacuum distillation. Useful concentrations of CMF in organic solvent are between 5 milligrams per milliliter to 1000 milligrams per milliliter, preferably between 30 milligrams per milliliter to 500 milligrams per milliliter.

The hydrochloric acid from this stage can be reconcentrated with dry hydrogen chloride gas and reused in subsequent runs. HCl gas is communicated through the aqueous phase liquid after being passed through above described apparatus so that the HCl content by mass is returned to at least 26% hydrochloric acid, to be used in conjunction or separately to achieve desired molarity for CMF production.

In the fourth stage of the process, the organic phase, which contains organic-soluble or suspended in the organic phase HTC and residual hydrochloric acid, is washed with an inorganic base dissolved in aqueous solution at or below the inorganic base's solubility limit in water to create a state of pH greater than or equal to seven. This solution is used at a minimum of 5% by volume of the total volume of the organic phase solution to wash the total volume of organic phase containing the CMF product. Excess hydrochloric acid is neutralized in this manner, thus limiting degradation at room temperature of CMF and limiting further HTC formation.

Inorganic bases useful in the present invention include but are not limited to bicarbonate and carbonate salts of alkali metals, including lithium, sodium, potassium, and cesium, and of alkaline earth metals, such as calcium, barium, magnesium, or combinations thereof. Concentrations of inorganic bases in aqueous solution useful in the present invention are from 0.1% to the respective solubility limit.

Material selection for apparatuses according to the present invention is important, since few materials are compatible with a mixture of a hydrochloric acid and organic solvents desired in the present invention. Suitable materials for the present invention which include, but are not limited to, Polypropylene, glass-filled polypropylene, Polytetrafluoroethylene (PTFE), Perfluoroalkoxy (PFA) resin, Fluorinated ethylene propylene (FEP), Polyethylene, Polyvinylidene fluoride (PVDF), Boro Silicate Glass, Viton fluoroelastomer, Ethylene chlorotrifluoroethylene (Halar) coated steel or Tantalum infused steel. These materials must be taken into account at every interface with liquids described here, including, but not limited to, tanks, vessels, tubing/piping, valves, pumps, fittings, unions, mixers, pressure dampeners, adapters or bushings, in that instance which both hydrochloric acid and organic solvents are present, material selection would include but would not be limited to Polypropylene, glass-filled polypropylene, Polytetrafluoroethylene (PTFE), Perfluoroalkoxy (PFA) resin, Fluorinated ethylene propylene (FEP), Polyethylene, Polyvinylidene fluoride (PVDF), Boro Silicate Glass, Viton fluoroelastomer, Ethylene chlorotrifluoroethylene (Halar) coated steel or Tantalum metal.

Phase separation includes liquid-gas, liquid-solid, gas-solid, liquid-liquid and solid-solid systems. The phase separation in this invention includes liquid-solid and liquid-liquid. When CMF is produced by the method of this invention, all phase separation is continuous because the materials (either dry bulk or fluids) that are being processed are continuously in motion.

Solid-liquid separation is a major unit operation that exists in almost every flow scheme related to chemical process industries. Depending on the properties of solid-liquid systems, various methods have been used. Filtration and centrifuge are the most commonly used methods in batch, semi-continuous and continuous modes.

Separation in liquid-liquid systems is most commonly accomplished by means of either gravity or a centrifuge. A key difference is whether the droplets which constitute the dispersed phase are large enough so that they rise or fall at a useful velocity. Liquid-liquid extraction, also known as solvent extraction and partitioning, is a method to separate compounds based on their relative solubility in two different immiscible liquids, usually water (aqueous phase) and an organic solvent (organic phase). It is an extraction of a substance from one liquid phase into another liquid phase.

EXAMPLE EMBODIMENTS

Example Apparatus.

Figure 1:
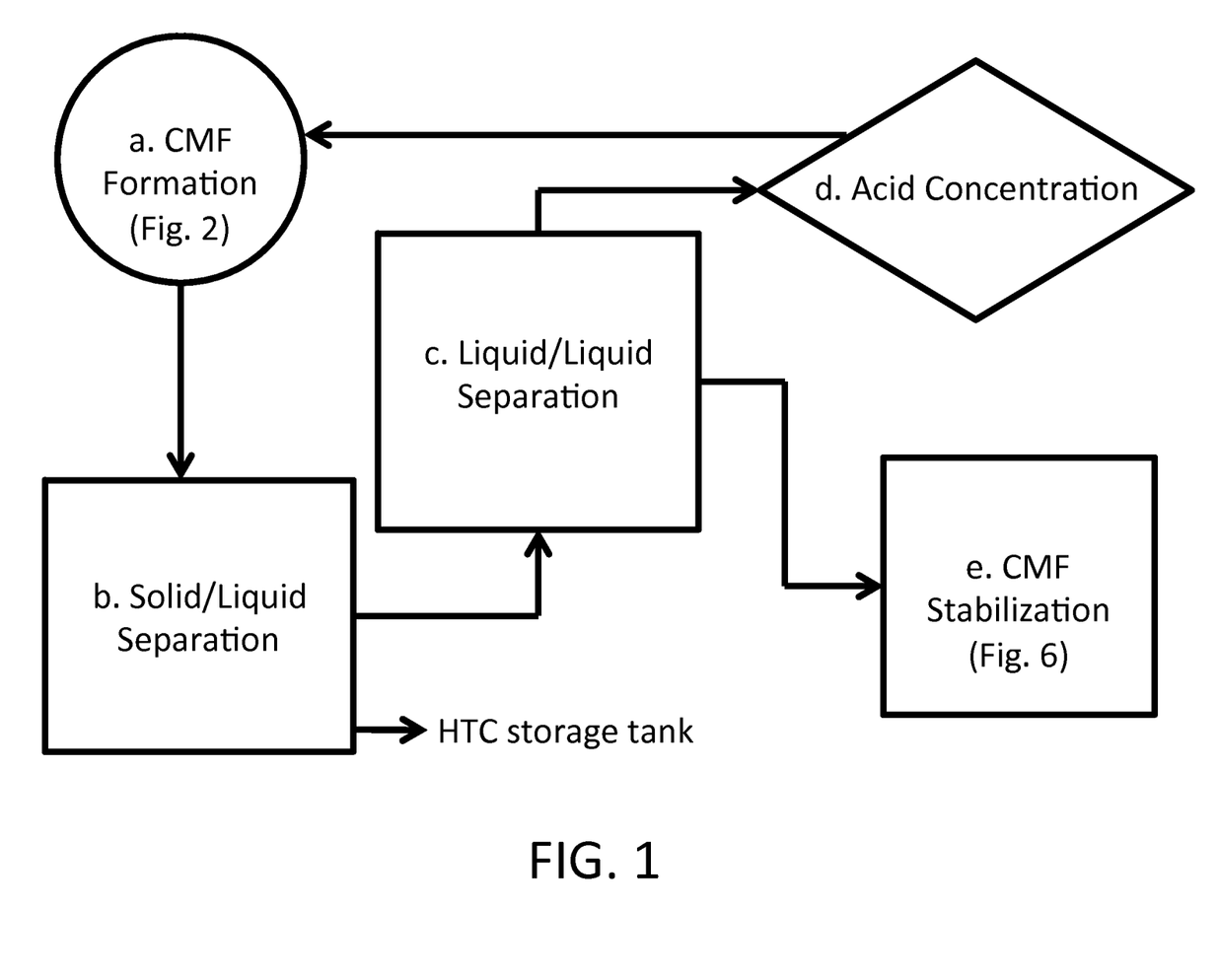
FIG. 1 is a schematic illustration of a process according to the present invention.

FIG. 1 is a schematic illustration of an example apparatus according to the present invention. A Reaction Vessel is provided, suitable to house a biphasic mixture, as described above. The biphasic mixture continuously flows through the reaction Vessel, where heat is added to it. From the reactor, the biphasic mixture which now contains CMF flows into a heat remover, where heat is removed from the biphasic mixture, thereby reducing the formation rate of HTC.

A Solid/Liquid Separation system is in constant fluid communication with the heat remover, and configured to continuously remove HTC created during CMF production in the previous stages. A system configured to perform subsequent washes of the material, fostering higher yields, is in constant fluid communication with the Solid/Liquid Separation system. The output of the subsequent washes comprises an acidic aqueous phase, and an organic phase. The organic phase, which contains CMF for concentration is treated with a basic solution to remove residual acid thereby preventing CMF degradation.

Additional information that can be useful in construction and operation of embodiments of the present invention can be obtained by review of the following, in connection with the teaching of the present disclosure: M. Mascal, U.S. Pat. No. 7,829,732 B2, 2010; M. Brasholz, K. von Känel, C. H. Hornung, S. Saubern and J. Tsanaktsidis, Green Chem., 2011, 13, 1114; M. Mascal and E. B. Nikitin, Angew. Chem., Int. Ed., 2008, 47, 7924; M. Mascal and E. B. Nikitin, ChemSusChem, 2009, 2, 859; M. Mascal and E. B. Nikitin, Green Chem., 2010, 12, 370. Each of the preceding is incorporated by reference herein.

An example method of production according to the present invention provides a method for the production of CMF, in which saccharides in a pure or crude form, hydrochloric acid, and an organic solvent (or mixture of organic solvents) are contacted by way of a continuous, biphasic-flow reactor assembly at a temperature from about 60 degree C. to about 200 degree C. and pressures from about 1 atmosphere to 10 atmospheres, such that CMF is produced.

The steps of an example method comprise:

Saccharide, or saccharides in a pure or crude form, are dissolved in hydrochloric acid, and at a set temperature and for a time, preferably two hours or less.

The acidic aqueous mixture and organic solvent (or mixture of organic solvents) are then continuously contacted together to form a biphasic mixture. Maintaining biphasic conditions in the reaction chamber is important to attain high yields. The term "biphasic" as used herein means having two distinguishable layers, one being a low pH "aqueous phase" and the other being an "organic phase" containing the above described organic solvent (or mixture of organic solvents) and any CMF created from the above reaction.

The biphasic mixture is then heated with an oven or other thermal energy device, such as a microwave, allowing for saccharides in a pure or crude form conversion to CMF.

To maintain the continuous biphasic flow, as described in the previous step, the pressure can be maintained such that the process temperature does not cause vaporization of the reactants or the reaction media. Pressures useful in the present embodiment are between 8 atmospheres and 11 atmospheres.

After a suitable reaction time, the temperature of the biphasic mixture is then reduced, for example by means of a heat remover, to slow the production of Hydrothermal Carbon (HTC). A useful reaction time for this embodiment is two minutes. When an appropriate temperature is reached, the biphasic mixture then continuously undergoes solid/liquid separation in order to remove HTC created during CMF production. Useful temperatures for this embodiment for solid/liquid separation is between 30 degrees C. and 40 degrees C.

The organic phase, which includes the CMF, can be separated continuously, semi-continuously, or in batches responsive to the manufacturer's preferences. Multiple subsequent solvent washes can be used to recover more CMF from the aqueous phase with an appropriate organic solvent which is immiscible with water.

The acidic aqueous phase can then be filtered, and the pH adjusted by the addition of dry hydrogen chloride gas to so that optimal acid concentration can be achieved, as described above.

The organic phase can then be treated as described above in the definition sections as "base wash".

Example Embodiment and Operation for a 5 kg of CMF/Day System

Fructose is fully dissolved in 32% hydrochloric acid at a ratio of 100 g/L and aged for a minimum of 45 minutes. This mixture represents the aqueous phase of the reaction.

Dichloromethane represents the organic phase. The organic phase and aqueous phase liquids, either separately or combined, are interfaced at a "T" or "Y" type union using ⅜" Perfluoroalkoxy (PFA) tubing in conjunction with PFA resin compression fittings. Here the biphasic interface is created at a ratio of approximately 1:1 (aqueous phase to organic phase). Upon converging at the biphasic interface, tubing, acting as the reaction vessel, is coiled and continuously used as a biphasic-flow reactor assembly in an oven (or heated in some other way, such as having resistance heating wire near the tubing) such that the continuous flow resides in the oven (or is otherwise heated) for approximately 2 minutes or where in the biphasic mixture temperature reaches at least 100 degrees C. to allow for CMF production. Upon exiting the oven, the tubing carrying the biphasic reaction mixture continuously enters a heat remover (e.g., a water bath type heat remover) that allows for dissipation of heat absorbed. Temperature is allowed to drop to between 30 degrees C. and 40 degrees C. during this time. A pressure regulation device can be used as to regulate pressure in the reaction vessel, for example to maintain pressure greater than 70 PSI.

HTC can then be removed by a sock type solid/liquid separation apparatus and the organic phase can be separated by gravity, while the aqueous phase can be filtered through a sock type filter, then communicated to a polyethylene tank, where Hydrogen Chloride gas can be bubbled into it by means of a perforated polypropylene tube to concentrate the acid to the original concentration (preferably 32% HCl by weight), so that it is suitable for reuse in the system as Aqueous Phase material for CMF production.

The base wash in this embodiment is done in the following manner: The organic phase is subjected to vacuum distillation until a concentration of approximately 300 milligrams per milliliter of CMF in DCM is reached. The concentrated CMF in DCM is washed at a 10:1 volume ratio of organic phase to basic aqueous solution. The aqueous solution is made by adding 100 g of sodium carbonate to 1.0 liter of water (0.94M) and the resulting aqueous solution has a pH of at least 7. Once the sodium carbonate is fully dissolved, the basic wash media (washing solution) is ready for use.

Previously, those skilled in the art would expect that a base wash would destroy CMF. However, the inventors have discovered that a base wash can remove a portion of HTC and increase the yield of the reaction. HTC is comprised of two components: polar and non-polar (hydrophilic and hydrophobic). The base wash can make the hydrophilic component more polar and thereby remove it into the aqueous phase. The HTC particles left in solvent-CMF phase predominantly contain hydrophobic moieties. It's the HTC that contains the polar moieties that reduce the reaction yield; the hydrophobic type is a lot less reactive toward CMF. To convert CMF to other products, that HTC with polar moieties needs to be removed or else it will reduce the yield of subsequent reactions substantially. There are other methods to separate the CMF from the dissolved HTC with the polar moieties, and they are lacking in their economic viability. If CMF is to be separated from the rest of the solvent by distillation, a portion of it will be destroyed by the polar portion of the remaining HTC. If CMF is to be separated from the remaining polar HTC by physical methods, a large proportion of the CMF will stay behind. If CMF is to be converted to another product, the polar portion of the remaining HTC will deteriorate the yield of the desired reaction. The base wash described herein overcomes these limitation of the prior approaches.

Example Embodiment for >100 kg CMF/Day System

Another example embodiment of the current invention can be scaled for much larger amounts, with monosaccharide inputs totaling 100 kg/day. This system can be driven by diaphragm-style pumps connected to polypropylene piping leading into High Density Polyethylene (HDPE) vessels. A tantalum reaction vessel can be utilized for more effective heat transfer. In this embodiment utilizing continuous separation and effective heat removal this embodiment would have the capability to be up scaled infinitely. Continuous separation discussed previously can be used, and Solid/Liquid separation can be utilized during HTC removal prior to Liquid/Liquid separation at aqueous and organic phase interface during CMF production as well.

DETAILED DESCRIPTION OF THE DRAWINGS

FIG. 1 is a schematic illustration of a process according to the present invention. A CMF production step or system feeds its output to a solid/liquid separation system. The solid output (HTC) is communicated to water wash and drying steps. The liquid output contains both the aqueous phase which is acidic (the acid used being hydrochloric acid) and the organic phase which contains the halogenated solvent (methylene chloride in this embodiment) and CMF. This liquid output is then communicated to a liquid/liquid step or system. The aqueous output of the liquid/liquid Separation system (hydrochloric acid and a negligible amount of HTC impurities) is communicated to an acid concentration step or system, which in turn communicates concentrated acid, about equal to the optimal acid concentration, back to the CMF Formation step or system. The chlorinated solvent output of the liquid/Liquid Separation system is communicated to a CMF Stabilization step or system (also referred to as the "base wash", as described above). The stabilized CMF is then concentrated by a simple distillation step or system, CMF may also be used as is in the form of a solution in an organic solvent responsive to the manufacturer's preferences. The chlorinated solvent is recovered from the distillation step and is communicated back to the CMF formation step.

Figure 2:
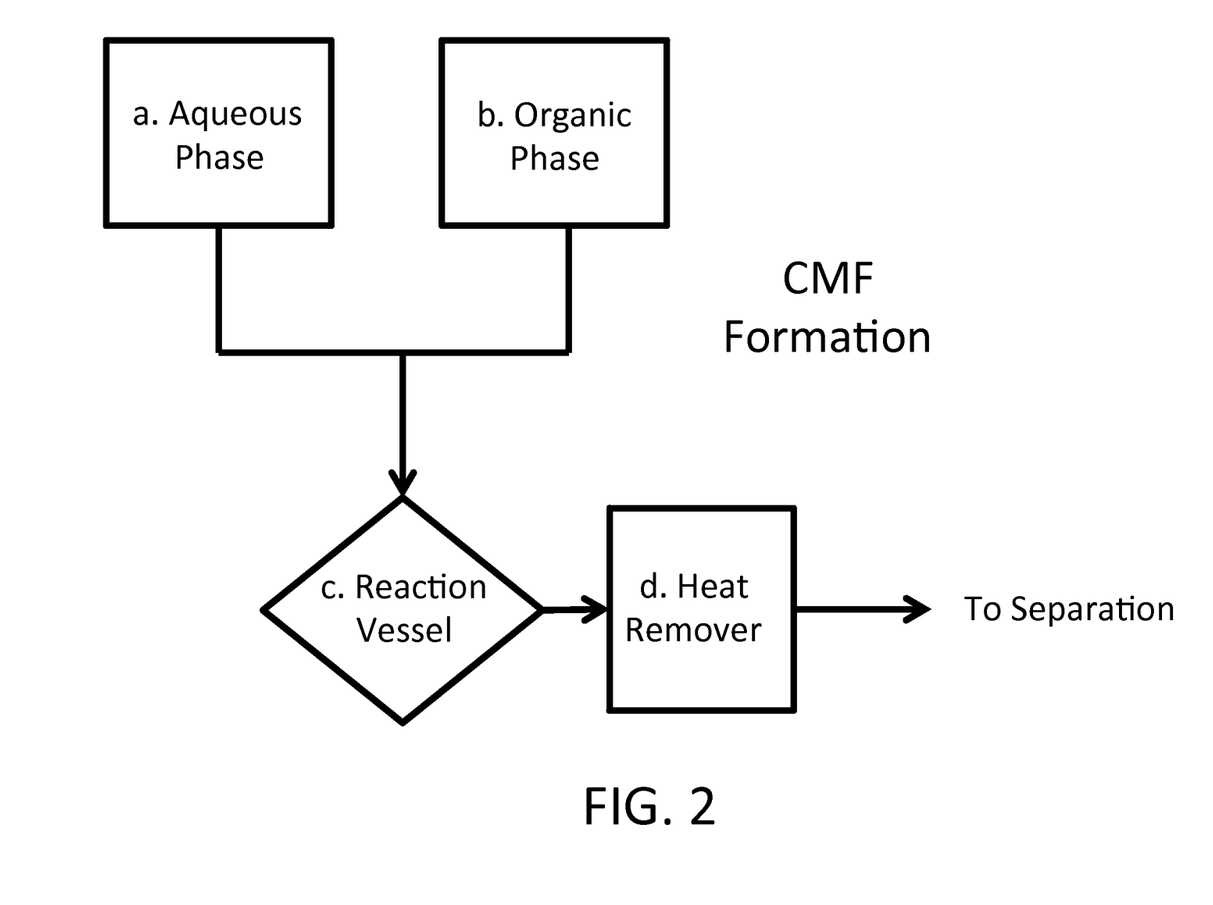
FIG. 2 is a schematic illustration of the CMF formation phase of the process illustrated in FIG. 1.

CMF is created under biphasic (organic solvent/aqueous) conditions in a reaction vessel, as in FIG. 2. Solid HTC is separated from the liquid media and communicated to a storage tank. Acidic aqueous phase is separated and removed from the organic phase. The organic phased contains the product (CMF). The CMF in the organic phase undergoes stabilization as in FIG. 5. Aqueous phase is concentrated for re-use in the system at the beginning of the CMF formation as in FIG. 5.

FIG. 2 is a schematic illustration of the CMF Formation phase of the process illustrated in FIG. 1. Here the acidic aqueous phase and the chlorinated solvent (methylene chloride in this embodiment) in the organic phase are communicated to a union where a biphasic condition is created. Once this biphasic flow enters the reaction vessel CMF and HTC begin to form. Following the reaction vessel, the heat remover then reduces the temperature of the reacted fluid to 30 degrees C.-40 degrees C. Biphasic flow is then continuously communicated to the phase separation step as shown in FIG. 3.

A suitable reaction vessel can comprise coiled PFA tubing. A suitable heat remover can be a water bath type. Separation can be completed mechanically or by gravity. Biphasic flow will exist from the organic phase and aqueous phase interface to the separation step. The aqueous phase can comprise 32% HCl and monosaccharides at 100 g/L aged for at least 45 minutes. The organic phase can comprise dichloromethane. The reaction vessel can have a residence time of approximately 2 minutes at approximately 100 C and 100 PSI. The heat remover can be capable of sustaining >100 PSI and 100 C under chemical conditions outlined above. Preferably temperature will be reduced >30 C during the heat remover step.

Figure 3:
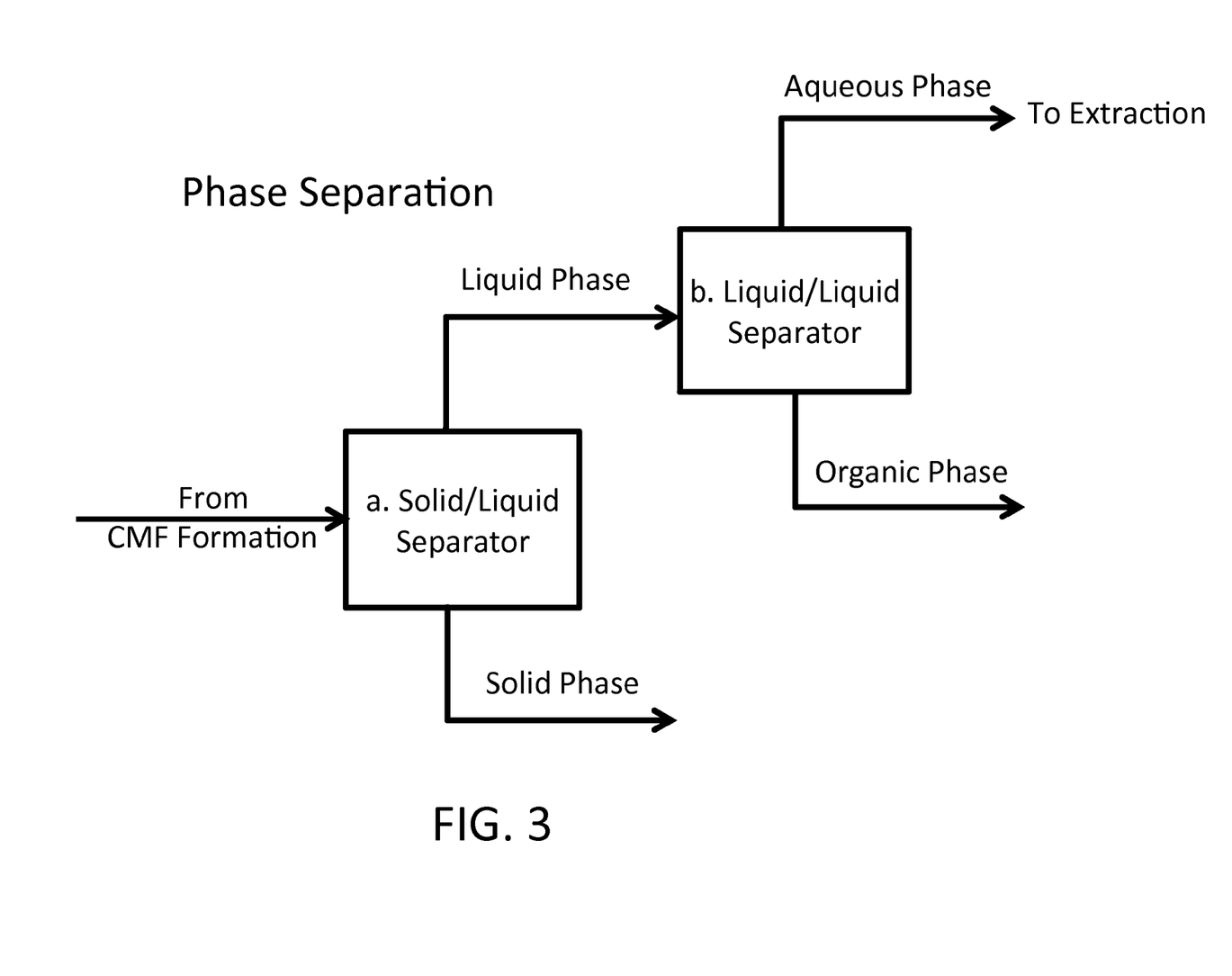
FIG. 3 is a schematic illustration of the Solid/Liquid Separation phase of the process illustrated in FIG. 1.
Figure 6:
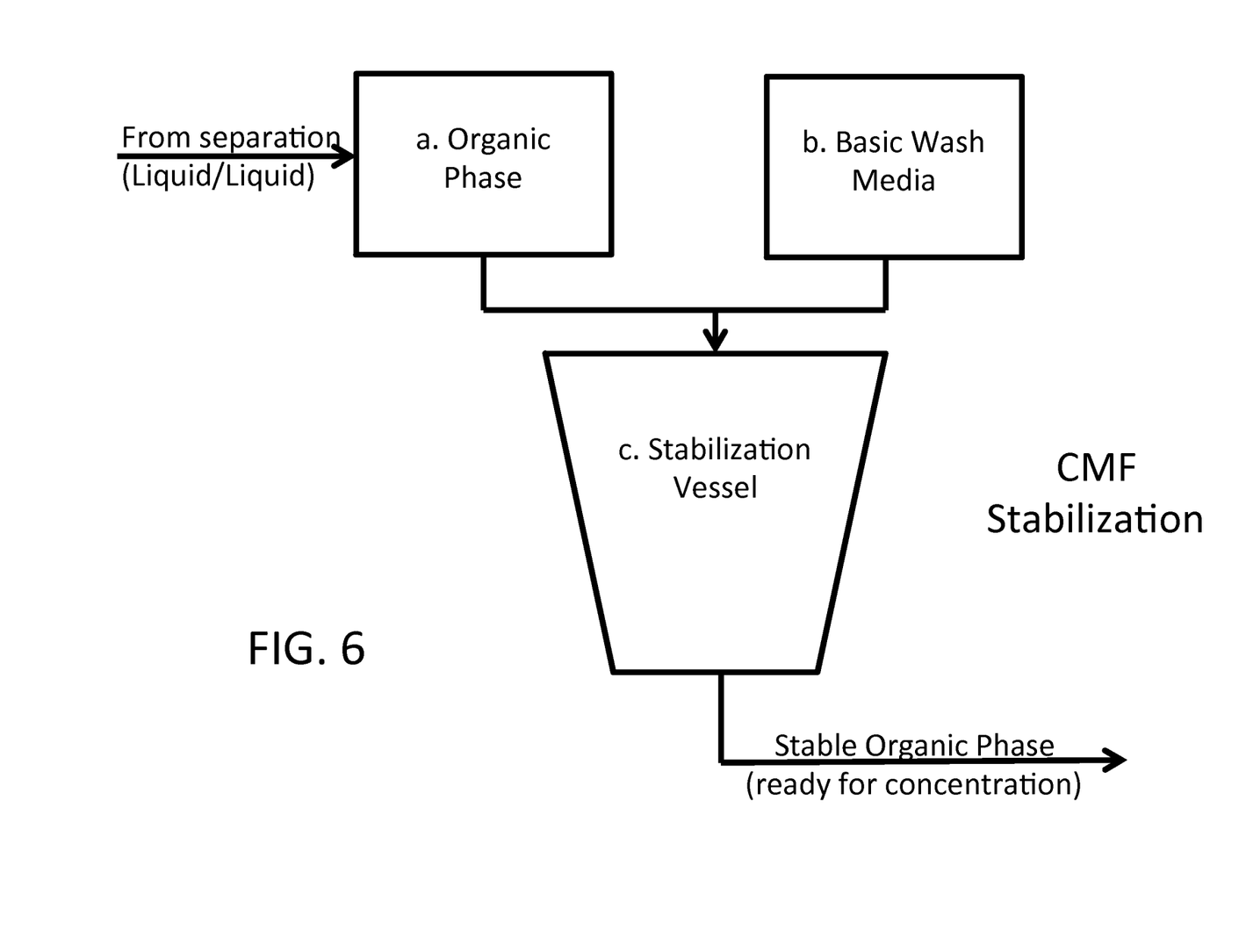
FIG. 6 is a schematic illustration of the CMF Stabilization phase of the process illustrated in FIG. 1.
Figure 7:
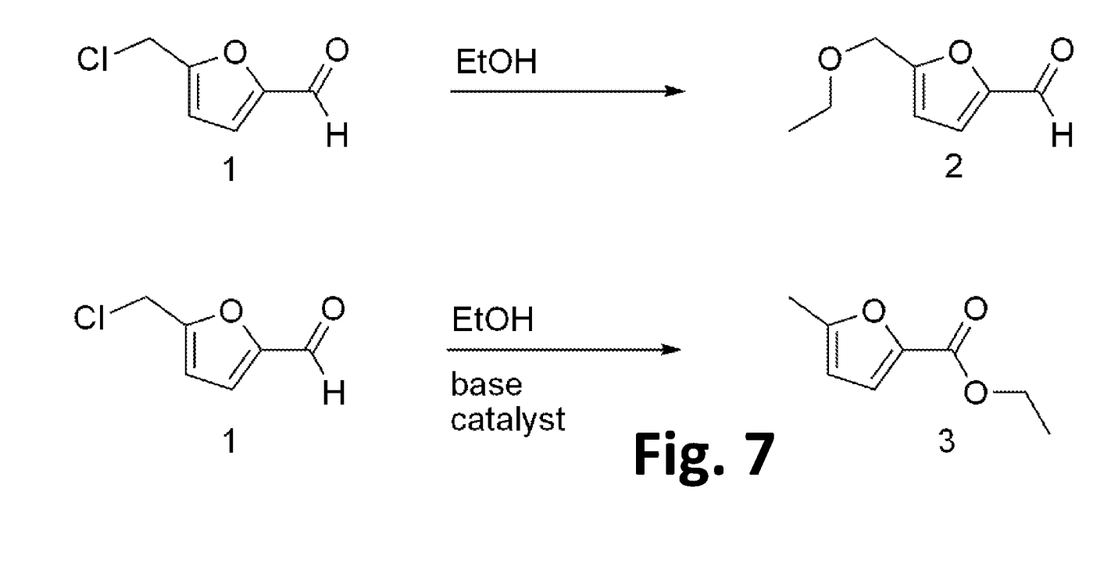
FIG. 7 illustrates a proposed catalytic cycle mechanism in accord with the present invention, along with that of known α-chloroaldehydes with NHC catalysis.
Figure 8:
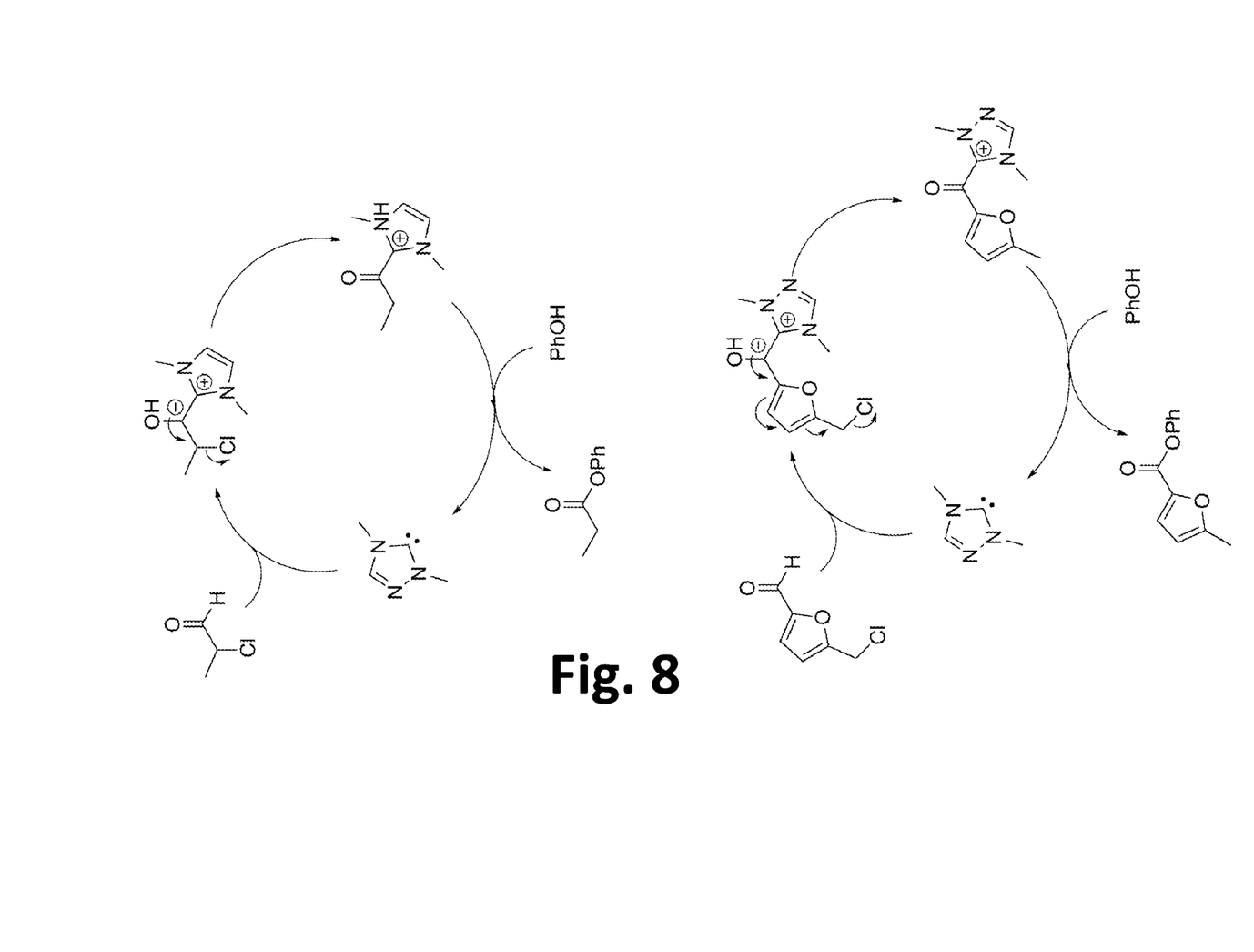
FIG. 8 illustrates representative precursor salts of N-heterocyclic carbene catalysts, and their deprotonation with bases.
Figure 9:
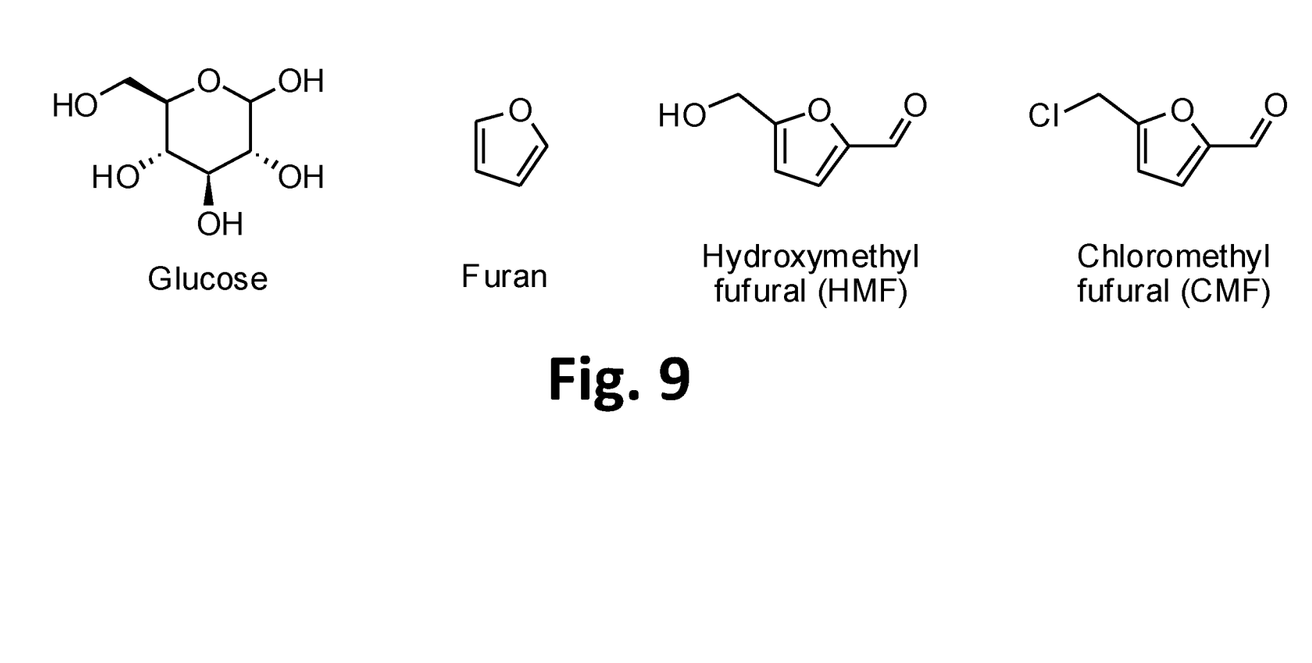
FIG. 9 is a schematic illustration of glucose and derived molecules.
Figure 10:
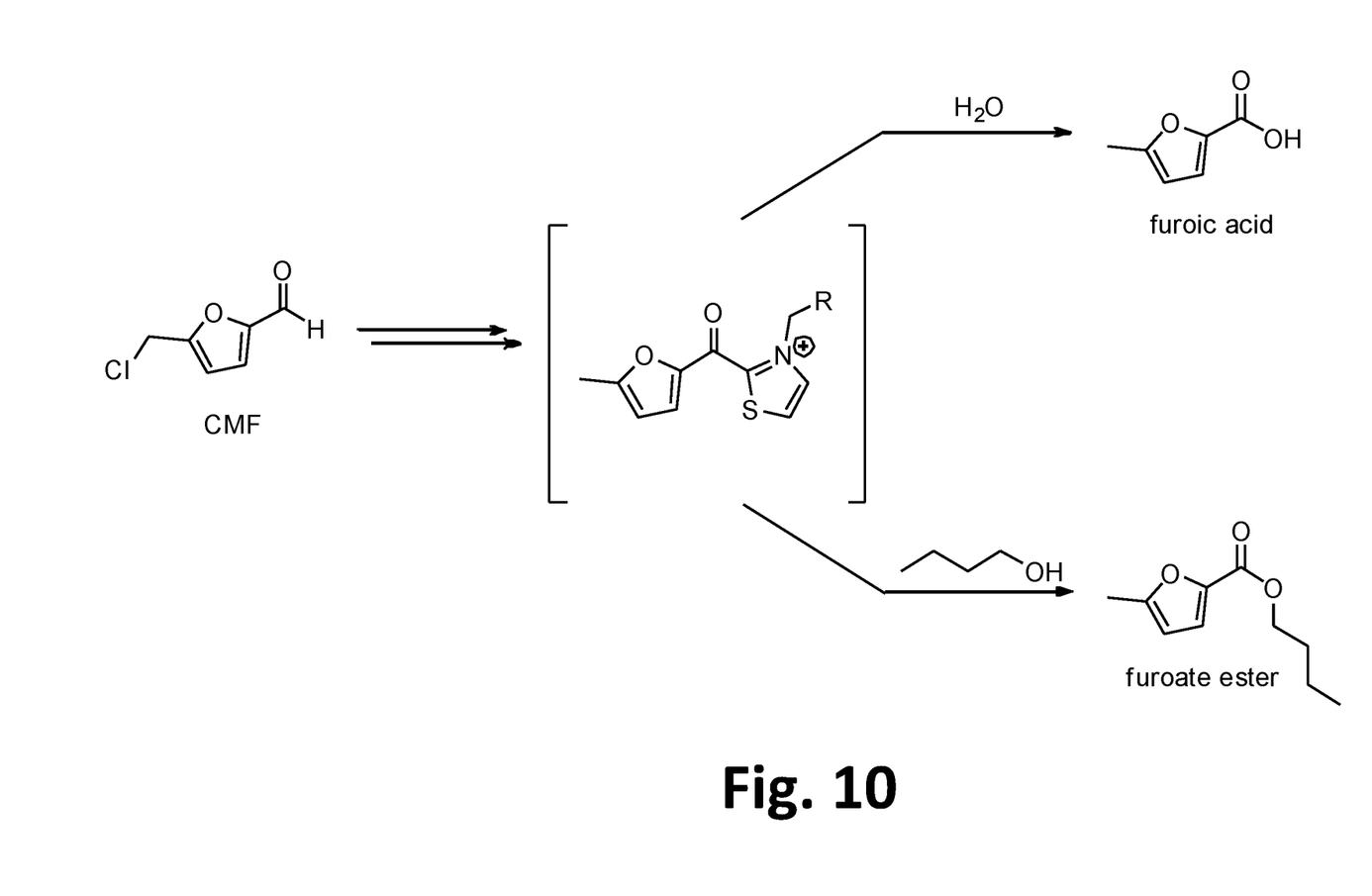
FIG. 10 is a schematic illustration of disparate reactivity of the acyl intermediate to provide furoate esters.

FIG. 3 is a schematic illustration of the Solid/Liquid Separation phase of the process illustrated in FIG. 1. Here continuous separation of two phases occurs: solid-liquid and liquid-liquid. Each phase is communicated through the phase separators. The separated solid phase and organic phase (methylene chloride in this embodiment) are proceeded for further purification (FIG. 6). The aqueous phase (32% aqueous Hydrochloric Acid) is proceeded for extraction (FIG. 4).

The solid/liquid and liquid/liquid are separated through the phase separators. The separated solid phase and organic phase (heavy) are proceeded for further purification as in FIG. 6. The aqueous phase (light) is proceeded for extraction.

Figure 4:
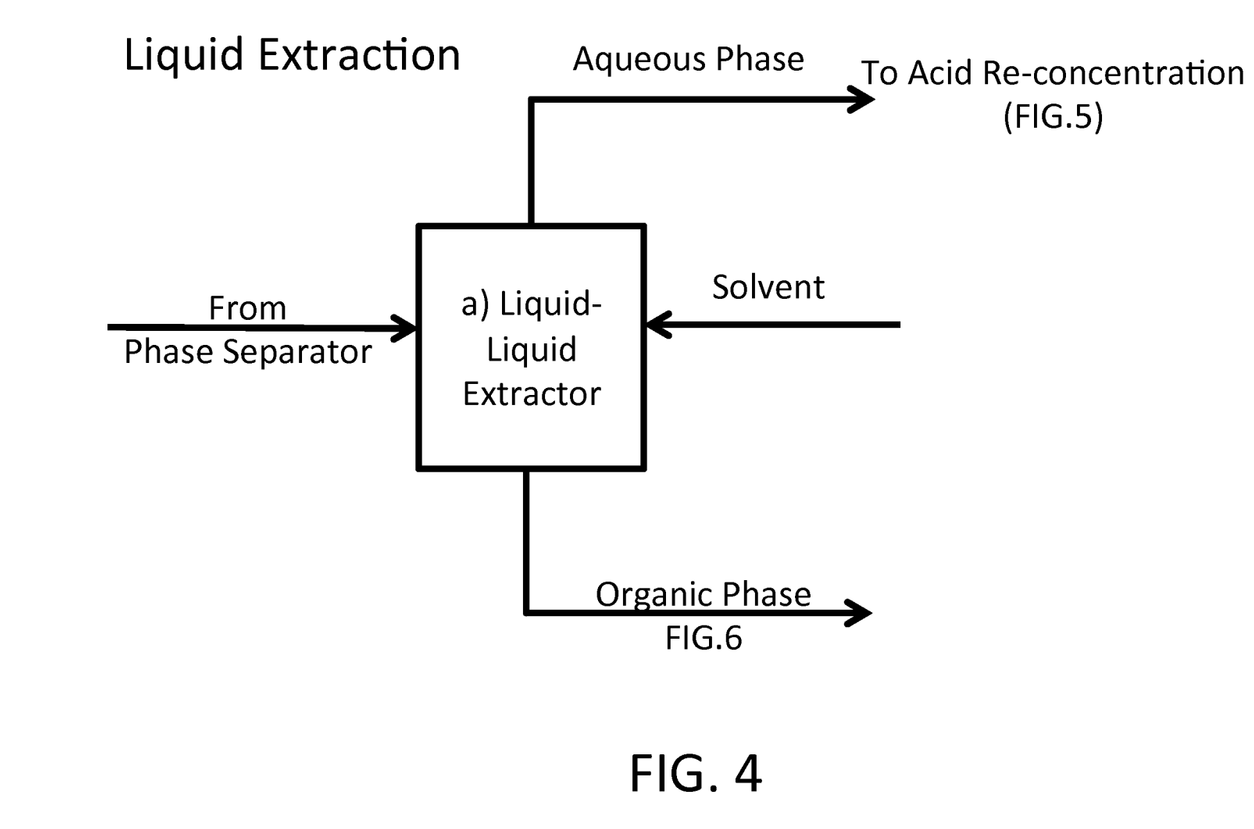
FIG. 4 is a schematic illustration of the Liquid/Liquid Separation phase of the process illustrated in FIG. 1.

FIG. 4 is a schematic illustration of the Liquid/Liquid Separation phase of the process illustrated in FIG. 1. Aqueous phase from phase separator (FIG. 3) and solvent are mixed in a liquid-liquid extractor. The separated organic phase (in the case of a chlorinated organic solvent such as methylene chloride in this embodiment) is proceeded for further purification (FIG. 6). The aqueous phase is proceeded for acid re-concentration (FIG. 5).

Aqueous phase from phase separator (FIG. 3) and solvent are mixed in a liquid-liquid extractor. The separated organic phase (heavy) are proceeded for further purification (FIG. 6). The aqueous phase (light) is proceeded for acid re-concentration (FIG. 5).

Figure 5:
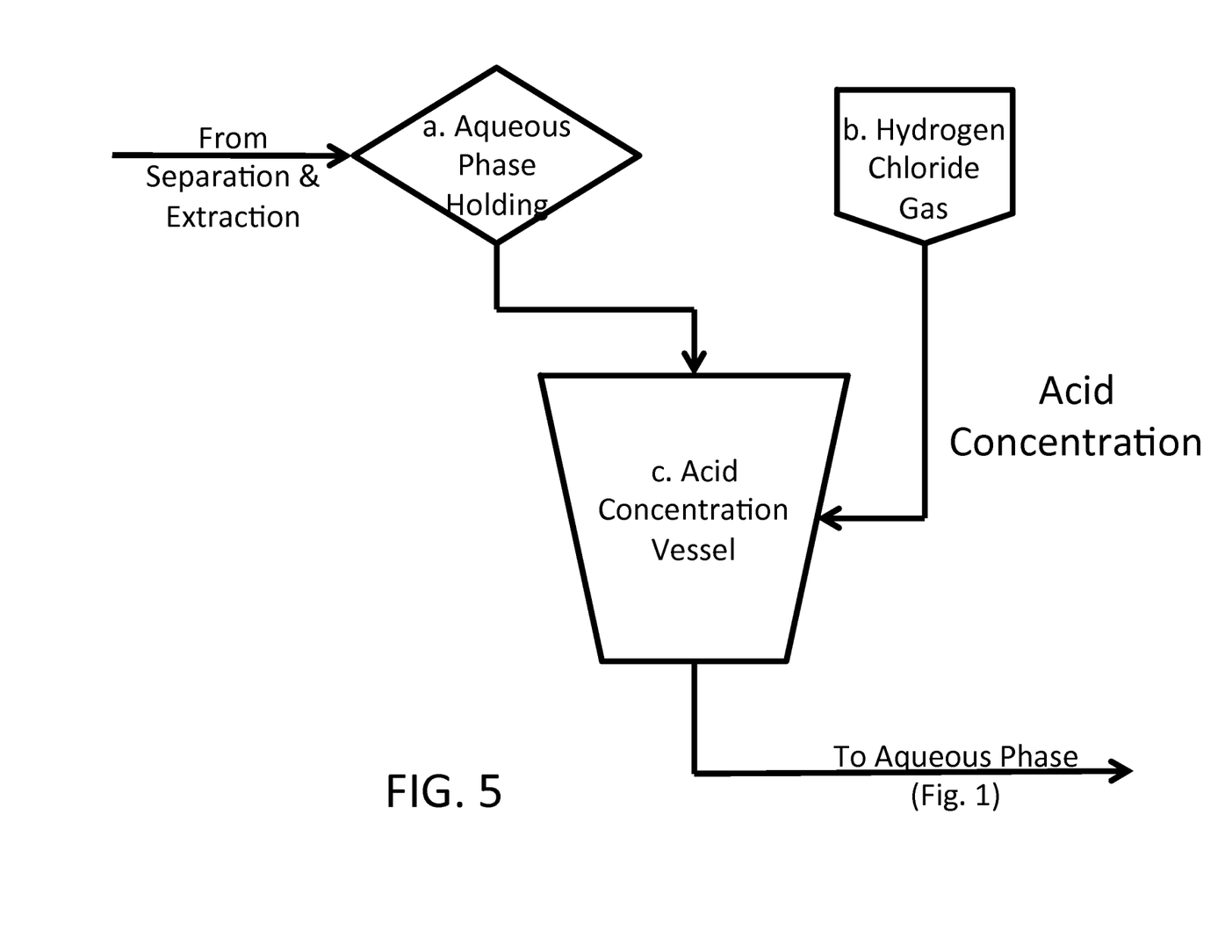
FIG. 5 is a schematic illustration of the Acid Concentration phase of the process illustrated in FIG. 1.

FIG. 5 is a schematic illustration of the acid concentration phase of the process illustrated in FIG. 1. The aqueous phase from the separation step (FIG. 4) is communicated from a holding vessel to a concentration vessel that contains a polypropylene diffuser or some method of communicating HCl gas into the aqueous phase so that the optimal molarity for the described process is achieved. Following the concentration step, the aqueous phase material will be suitable for reuse in the system starting at CMF formation (FIG. 2).

Hydrogen Chloride gas will be interfaced with aqueous phase via a diffusion type device. Acid Concentration vessel and diffuser can provide above atmospheric pressure for sustained time. Aqueous phase holding can comprise a vessel that will hold the processed and washed acid. Hydrogen Chloride gas is communicated by means of tubing capable of tolerating its corrosive nature. An Acid Concentration Vessel can house a polypropylene diffuser that will bubble the HCl gas through the used acid to return the acid to its original concentration.

FIG. 6 is a schematic illustration of the CMF Stabilization phase of the process illustrated in FIG. 1. The stabilization vessel contains two phases, heavier organic phase—in the case of a chlorinated organic solvent such as methylene chloride in this embodiment (containing CMF and solvent) and the lighter base wash media (washing solution described above). A two-layer interface, by means of a mixer or agitation, is allowed to settle and will be separated gravitationally or mechanically. The inventors have found that this step can be important to the stabilization and storage of CMF and also can remove some amount of HTC beyond the separation step.

Organic phase contains CMF and DCM solvent. Basic wash media contains 0.94 M sodium carbonate fully dissolved in water. The stabilization vessel can house a method of mixing a and b.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

We claim:

1. A method for the synthesis of an output consisting of an ester of 5-methyl-2-furoic acid from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system; wherein the reactive nucleophile is poly(vinyl alcohol) or a polymer composition containing poly(vinyl alcohol); and wherein the output consists of an ester of 5-methyl-2-furoic acid having an alkoxycarbonyl portion; and wherein the alkoxycarbonyl portion is poly(vinyl alcohol) or a polymer composition containing poly(vinyl alcohol).

2. A method for the synthesis of an output consisting of an ester of 5-methyl-2-furoic acid from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system; wherein the reactive nucleophile comprises one or more of (1) a linear aliphatic diol, (2) a branched aliphatic diol, and (3) a cyclic aliphatic diol; containing between 1 and 8 carbon atoms.

3. A method for the synthesis of an output consisting of an ester of 5-methyl-2-furoic acid from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system; wherein the reactive nucleophile comprises one or more of ethylene glycol, propylene glycol, diethylene glycol, and triethylene glycol.

4. A method for the synthesis of an output consisting of diester of 5-methyl-2-furoic acid from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system; wherein the output consists of a diester of 5-methyl-2-furoic acid having an alkoxycarbonyl portion; and wherein the alkoxycarbonyl portion comprises one or more of (1) a linear aliphatic chain, (2) a branched aliphatic chain and (3) a cyclic aliphatic; derived from a diol or glycol containing between 2 and 8 carbon atoms.

\* \* \* \* \*